US011311425B2

(12) United States Patent
Inoue et al.

(10) Patent No.: US 11,311,425 B2
(45) Date of Patent: Apr. 26, 2022

(54) MANUFACTURING METHOD AND MANUFACTURING APPARATUS FOR DISPOSABLE WEARABLE ARTICLE

(71) Applicant: ZUIKO CORPORATION, Osaka (JP)

(72) Inventors: Daisuke Inoue, Osaka (JP); Kouji Utani, Osaka (JP); Hideki Fujita, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 108 days.

(21) Appl. No.: 16/957,126

(22) PCT Filed: Jan. 8, 2019

(86) PCT No.: PCT/JP2019/000180
§ 371 (c)(1),
(2) Date: Jun. 23, 2020

(87) PCT Pub. No.: WO2019/142691
PCT Pub. Date: Jul. 25, 2019

(65) Prior Publication Data
US 2020/0345559 A1 Nov. 5, 2020

(30) Foreign Application Priority Data

Jan. 16, 2018 (JP) .............................. JP2018-004844

(51) Int. Cl.
*A61F 13/15* (2006.01)
*B26D 1/40* (2006.01)
(Continued)

(52) U.S. Cl.
CPC .. *A61F 13/15804* (2013.01); *A61F 13/15723* (2013.01); *A61F 13/15764* (2013.01);
(Continued)

(58) Field of Classification Search
None
See application file for complete search history.

(56) References Cited

U.S. PATENT DOCUMENTS

2003/0084767 A1  5/2003 Tanaka et al.
2008/0289468 A1  11/2008 Nakakado et al.
(Continued)

FOREIGN PATENT DOCUMENTS

JP  2003-199790 A  7/2003
JP  2007-260875 A  10/2007
(Continued)

OTHER PUBLICATIONS

International Search Report Issued in PCT/JP2019/000180 dated Apr. 16, 2019.

*Primary Examiner* — Barbara J Musser
(74) *Attorney, Agent, or Firm* — Renner, Otto, Boisselle & Sklar, LLP

(57) ABSTRACT

In order to manufacture a wearable article of the first size, the introduction velocity is set to the first introduction velocity having a high velocity and the arrangement velocity is set to the first the arrangement velocity having a high velocity. In order to manufacture wearable article of the second size having a shorter length in the carrying direction than that of the first size, the introduction velocity is set to the second introduction velocity lower than the first introduction velocity and the arrangement velocity is set to the second arrangement velocity lower than the first the arrangement velocity and the drum velocity is set to a fixed velocity regardless of the size.

8 Claims, 7 Drawing Sheets

(51) Int. Cl.
*B65H 20/12* (2006.01)
*B65H 35/08* (2006.01)

(52) U.S. Cl.
CPC ............... *B26D 1/40* (2013.01); *B65H 20/12* (2013.01); *B65H 35/08* (2013.01)

(56) References Cited

U.S. PATENT DOCUMENTS

2015/0024919 A1  1/2015  Shimada
2015/0223992 A1  8/2015  Maehara et al.

FOREIGN PATENT DOCUMENTS

| JP | 2008-035872 A | 2/2008 |
| JP | 2013-255624 A | 12/2013 |
| WO | WO 2005-075163 A1 | 8/2005 |
| WO | WO 2013-157533 A1 | 10/2013 |
| WO | WO 2014-006834 A1 | 1/2014 |

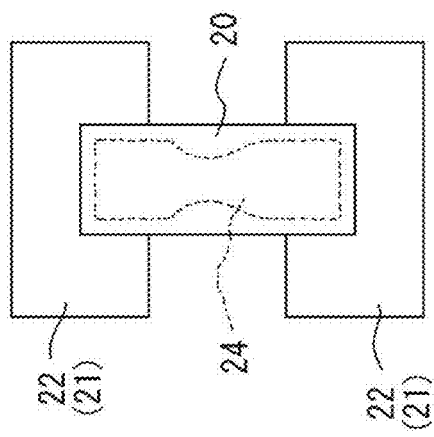
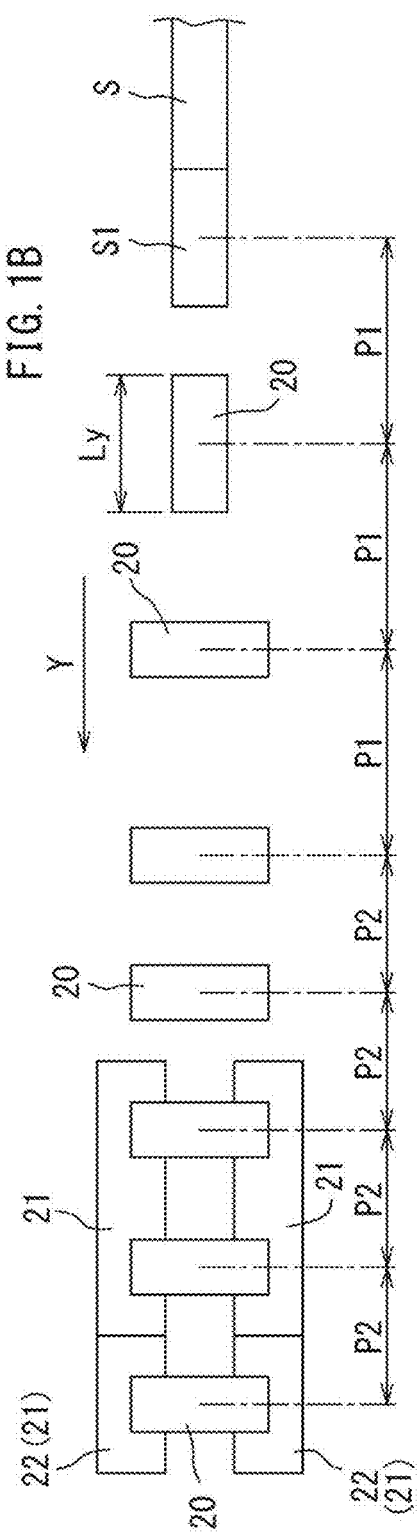

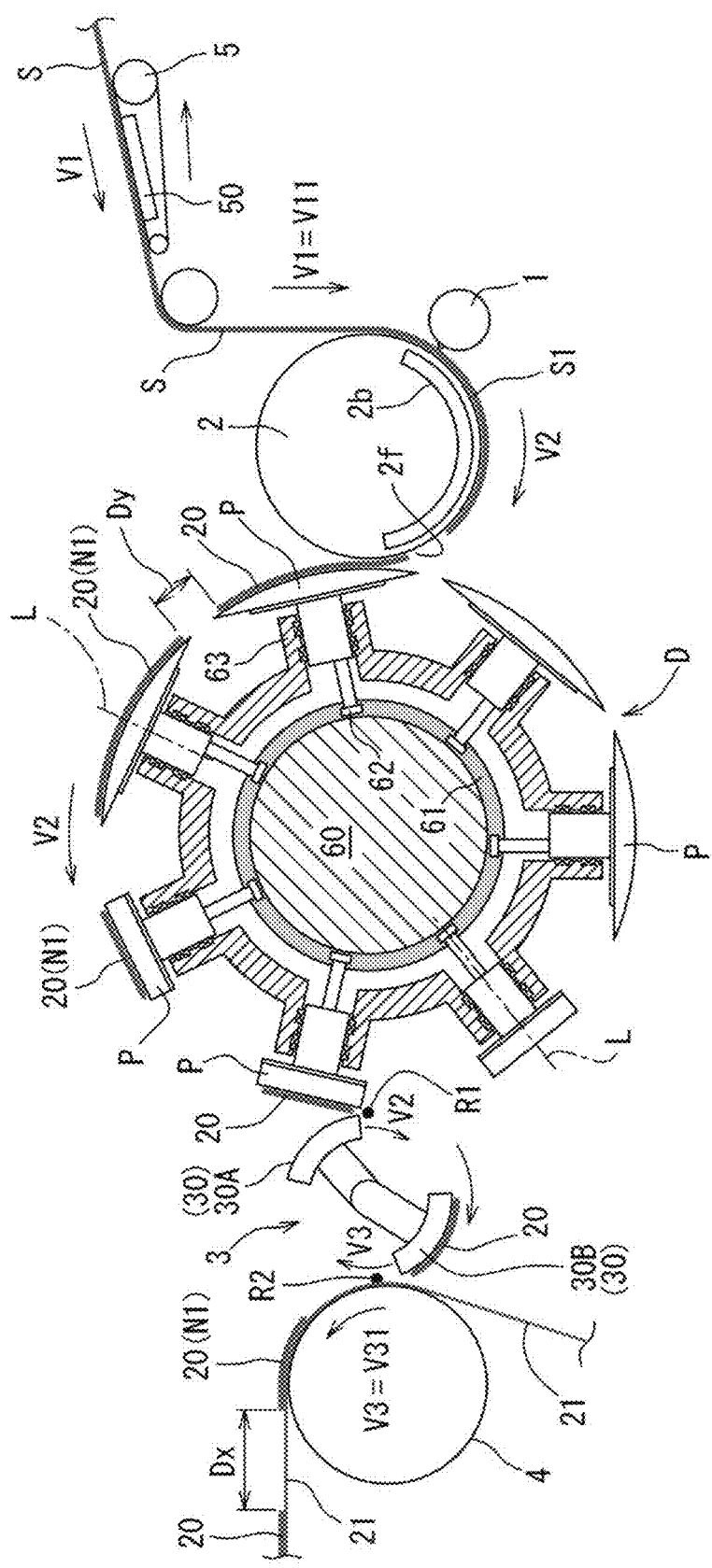

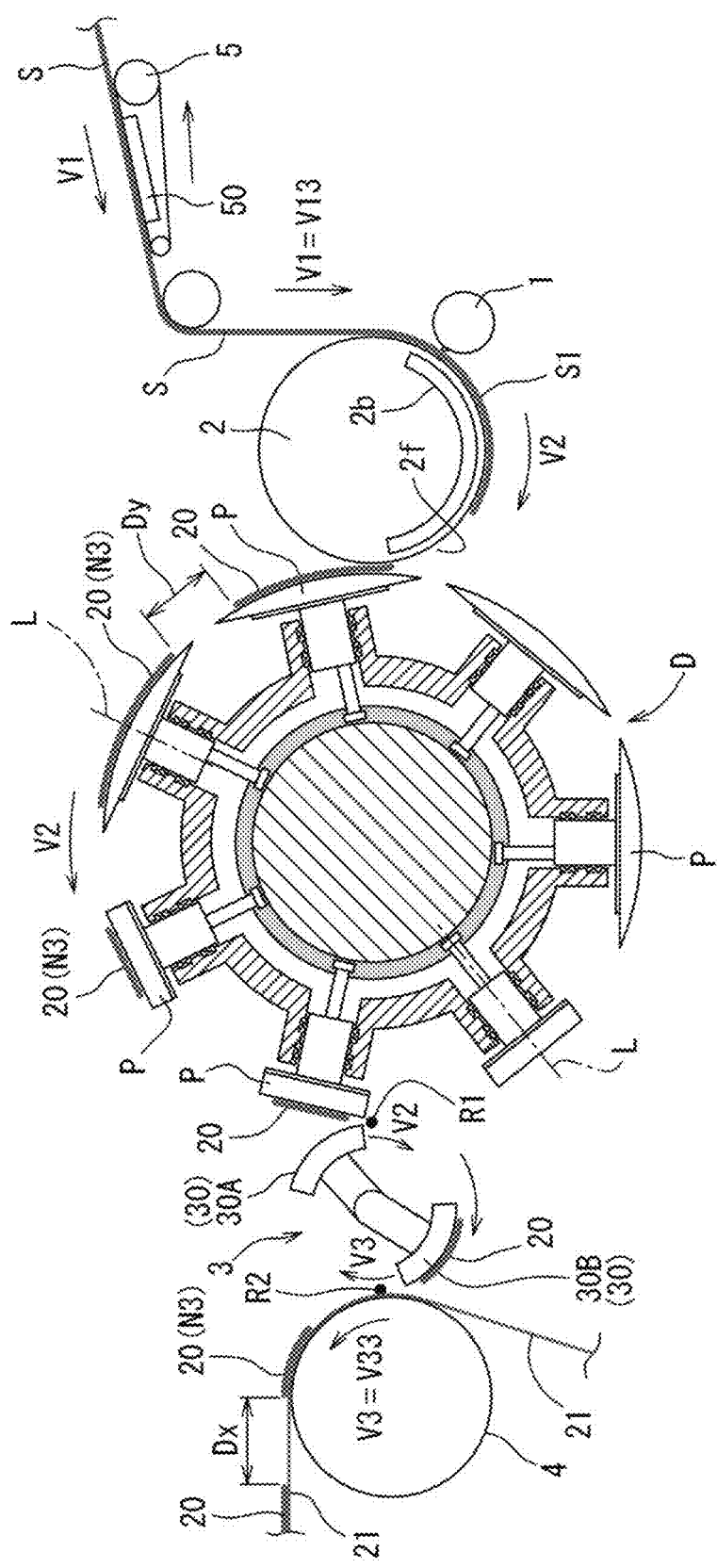

MANUFACTURING METHOD AND MANUFACTURING APPARATUS FOR DISPOSABLE WEARABLE ARTICLE

TECHNICAL FIELD

The present invention relates to a manufacture method and a manufacture apparatus of a disposable wearable article.

BACKGROUND ART

Regarding this type of manufacture of wearable articles, a method has been known according to which a so-called cut-and-slip procedure is used to cut sheet pieces out of a continuous sheet to arrange the respective cut sheet pieces on a continuous web with an increased interval among the sheet pieces (patent document 1).

CITATION LIST

Patent Literature

[The first patent document] JP2007-260875 A
[The second patent document] WO2005/075163 A
[The third patent document] WO2014/006834 A

SUMMARY OF INVENTION

Another method has been known according to which sheet pieces are received by retention pads on a rotating drum and the interval among the sheet pieces is increased by increasing the rotation velocity of the retention pads (patent documents 2 and 3).

In the case of this method, however, a mechanism is required to accelerate the retention pads. Furthermore, the retention pad has thereon an anvil to cut the sheet on the retention pads, which causes an increased inertia, causing a difficulty in the control.

Thus, it is an objective of the present invention to provide a manufacturing method and a manufacturing apparatus for a disposable wearable article for which no need is required to change the drum due to a change of a product size and the control is simple.

The manufacturing method of the present invention is a method for manufacturing a disposable wearable article in which an absorbing body overlaps an external material, the method including;

an introduction step of introducing a continuous laminated body S, which extends in a carrying direction, to an anvil roll 2 at an introduction velocity V1, the continuous laminated body S being to be used as absorbing bodies 20;

a slip step of carrying the continuous laminated body S at the introduction velocity V1, the slip step being performed by sucking a tip end S1 of the continuous laminated body S on a peripheral surface 2f of the anvil roll 2 rotating at a drum velocity V2 higher than the introduction velocity V1, with the tip end S1 of the continuous laminated body S slipping over the peripheral surface 2f of the anvil roll 2;

a cutting step of intermittently cutting the tip end S1 of the continuous laminated body S on the anvil roll 2 to thereby sequentially obtain the absorbing bodies 20;

a separation step of carrying the absorbing bodies 20, which have been cut in the cutting step, at the drum velocity V2 along the peripheral surface 2f of the anvil roll 2 to thereby separate the absorbing bodies 20 from the continuous laminated body S in the carrying direction;

a first transfer step of sequentially transferring the absorbing bodies 20, which have been separated in the separation step, from the anvil roll 2 to respective retention pads P of a turn drum D;

a posture change step of allowing the retention pads P of the turn drum D to rotate around an axis line DL of the turn drum D at a fixed velocity that equals the drum velocity V2, the posture change step allowing each of the retention pads P on the turn drum D to turn around a normal line L of the turn drum D to thereby change a posture of the absorbing bodies 20 together with the retention pads P;

a second transfer step of transferring the absorbing bodies 20 from the retention pads P of the turn drum D to respective velocity-changeable pads 30A and 30B of a velocity-changeable roller 3 at a receiving position R1 at the drum velocity V2;

a velocity change step of changing a velocity of the velocity-changeable roller 3 from the drum velocity V2 to an arrangement velocity V3 until the velocity-changeable roller 3 reaches a delivery position R2 from the receiving position R1;

a carrying step of allowing a carrying device 4 to carry an external material 21 at the arrangement velocity V3; and an arrangement step of sequentially arranging, at the delivery position R2, the absorbing bodies 20 over the exterior material 21 carried by the carrying device 4.

On the other hand, the manufacturing apparatus of the present invention is an apparatus for manufacturing a disposable wearable article in which an absorbing body overlaps an exterior material, the apparatus including:

a first carrying device 5 configured to carry a continuous laminated body S, which extends in a carrying direction, at an introduction velocity V1, the continuous laminated body S being to be used as absorbing bodies 20;

an anvil roll 2 rotating at a drum velocity V2 higher than the introduction velocity V1, the anvil roll 2 being configured to suck a tip end S1 of the continuous laminated body S on a peripheral surface 2f of the anvil roll 2 while to allow the tip end S1 of the continuous laminated body S to slip over the peripheral surface 2f, thereby carrying the continuous laminated body S at the introduction velocity V1, the anvil roll 2 being configured to carry absorbing bodies 20, which are obtained by intermittently cutting the tip end S1 of the continuous laminated body S, along the peripheral surface 2f at the drum velocity V2 higher than the introduction velocity V1 to thereby separate the absorbing bodies 20 from the continuous laminated body S in the carrying direction;

a cutter 1 configured to intermittently cut the tip end S1 of the continuous laminated body S on the anvil roll 2 to thereby sequentially generate the absorbing bodies 20;

a turn drum D configured to sequentially receive the absorbing bodies 20 from the anvil roll 2 via respective retention pads P of the turn drum D, the turn drum D being configured to carry the absorbing bodies 20 at a fixed velocity that equals the drum velocity V2 while each of the retention pads P turns around a normal line L of the turn drum D to thereby change a posture of the absorbing bodies 20 together with the retention pads P;

a second carrying device 4 configured to have an arrangement velocity V3 and to carry an exterior material 21; and a velocity-changeable roller 3 configured to receive the absorbing bodies 20 from the retention pads P of the turn drum D via respective velocity-changeable pads 30A and 30B of the roller 3 at a receiving position R1, the velocity-changeable pads 30A and 30B being configured to transfer, at a delivery position R2, the absorbing bodies 20 to the exterior material 21 carried by the second carrying device 4.

According to the present invention, a first-size wearable article and a second-size wearable article having a shorter length in the carrying direction than that of the first-size wearable are manufactured in the manner as described below.

When the first-size wearable article N1 is manufactured, the introduction velocity V1 is set to a first introduction velocity V11 having a high velocity, and the arrangement velocity V3 is set to a first arrangement velocity V31 having a high velocity;

when the second-size wearable article N2 is manufactured, the introduction velocity V1 is set to a second introduction velocity V12 lower than the first introduction velocity V11, and the arrangement velocity V3 is set to a second arrangement velocity V32 lower than the first arrangement velocity V31; and the drum velocity V2 is set to a fixed velocity regardless of the size of the wearable article.

Furthermore, a wearable article N3 of the third size having a length in the carrying direction shorter than that of the second-size wearable article is manufactured in the manner as described below.

Specifically, when the third-size wearable article N3 is manufactured, the introduction velocity V1 is set to a third introduction velocity V13 lower than the second introduction velocity V12, the drum velocity V2 is set to a fixed velocity regardless of the size of the wearable article, and the arrangement velocity V3 is set to a third arrangement velocity V33 lower than the second arrangement velocity V32.

As described above, according to the present invention, the introduction velocity V1 and the arrangement; velocity V3 are set; to respective velocities depending on the size of the wearable article. The drum velocity V2 of the turn drum D is set to a fixed velocity regardless of the size.

Thus, the turn drum D having a plurality of retention pads P has a small inertia and the drum velocity V2 of the turn drum D does not require acceleration and deceleration.

Thus, the present invention provides a manufacturing method and a manufacturing apparatus for a disposable wearable article, in which a drum replacement due to a change in the product size is not required and the drum control is easy.

BRIEF DESCRIPTION OF DRAWINGS

FIG. 1A is a developed view illustrating one example of a wearable article according to the present invention. FIG. 1B is a plan view illustrating one example of the manufacture method of the wearable article.

FIG. 2 is a schematic view illustrating the layout of the manufacture apparatus of the wearable article.

FIG. 7 is a schematic view illustrating the layout in the case where the wearable article of the third size is manufactured.

DESCRIPTION OF EMBODIMENTS

Figure 3A:
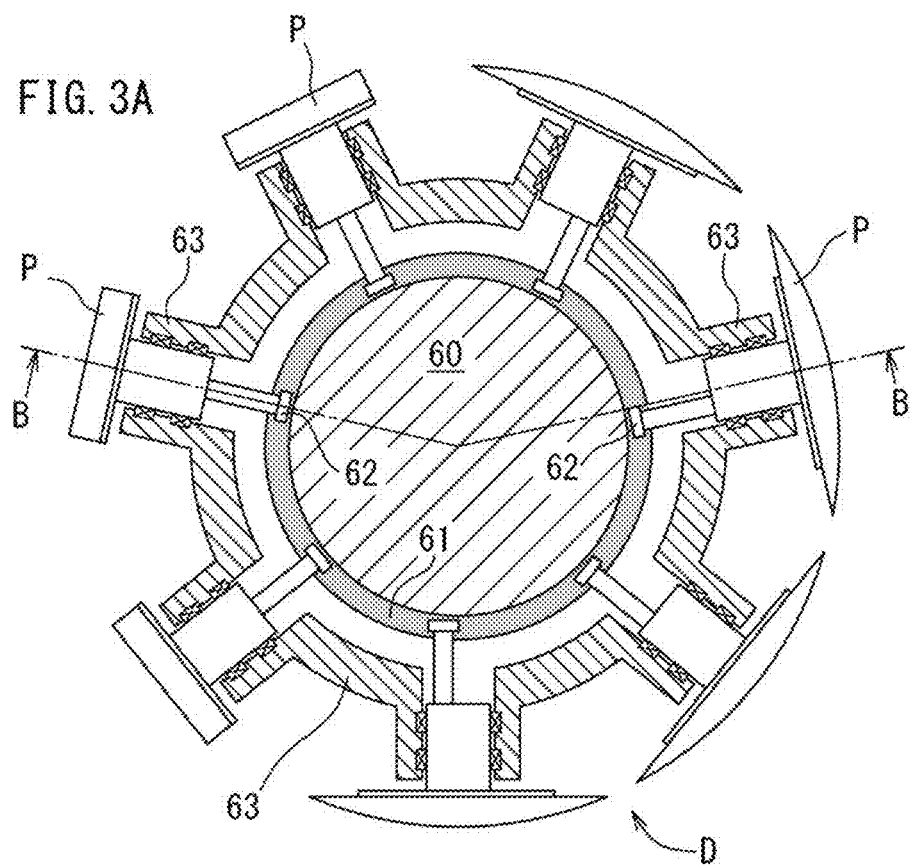
FIG. 3A is a schematic cross-sectional view of a turn drum.

According to the present invention method, the drum velocity V2 is further preferably set, regardless of the size of the wearable article, to a fixed velocity higher than the introduction velocity V1 and the arrangement velocity V3.

In this case, the drum velocity V2 is high. Thus, different sizes of wearable article will be manufactured by simply changing the introduction velocity V1 within a velocity range smaller than the drum velocity V2 based on a longitudinal length of an absorbing body 20 and by simply changing the arrangement velocity V3 within the velocity range based on a girth length of an external material 21.

According to the present invention apparatus, preferably, the velocity-changeable roller 3 includes: a pair of first velocity-changeable pads 30A retaining both ends in a longitudinal direction of a precedent absorbing body 20 among the absorbing bodies 20; and a pair of second velocity-changeable pads 30B retaining both ends in the longitudinal direction of a subsequent absorbing body among the absorbing bodies 20.

Specifically, one pad of a pair of first (or second) velocity-changeable pads is used to retain one end in the longitudinal direction of an absorbing body and another pad of the pair of first (or second) velocity-changeable pads is used to retain the other end in the longitudinal direction of the absorbing body.

In this case, each pair of velocity-changeable pads 30A and 30B retains both ends in the longitudinal direction of the corresponding absorbing body 20. Thus, the velocity-changeable pads 30A and 30B are configured to easily fit the shape of the respective retention pads P when receiving the absorbing body 20, thereby providing a smooth delivery.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

The following section will describe an embodiment of the present invention based on the drawings.

First, prior to the explanation of the manufacture method and apparatus, the following section will describe an example of a wearable article that can be manufactured by the manufacture method.

As shown in FIG. 1A, this diaper includes an absorbing body 20 and a pair of exterior materials 21, 21 to which the body 20 is joined.

The body 20 is configured, when the diaper is worn, to cover a part of a front torso region, a crotch region, and a part of a rear circumference region of a wearer.

The body 20 may include, for example, a pair of cuffs (leak-proof walls (not shown)) having a contact with the surface of the wearer, a liquid-permeable top sheet, an absorbing core 24 absorbing liquid, and a liquid-impermeable back sheet. The top sheet and the back sheet may have therebetween the core 24.

In the example of FIG. 1A, the absorbing body 20 is provided between a front torso member 22 and a rear torso member 22. Specifically, an end of a front section of the absorbing body 20 in the vertical direction (longitudinal direction) is adhered to the front torso member 22. On the other hand, an end of the back section of the absorbing body 2 in the vertical direction is adhered to the rear torso member 22.

The front and rear torso members 22 constitute the exterior material 21 and are obtained by cutting a continuous laminated body. Each of the respective torso members 22 may be a laminated body obtained by mutually laminating elastic members and a plurality of nonwoven fabrics.

It is noted that the exterior material 21 may not be divided to the front and rear torso members 22, 22, or instead may be a so-called T-shaped diaper.

Next, the following section will describe one example of the manufacture apparatus. As shown in FIG. 2, this manufacture apparatus includes a conveyor 5 (one example of the first carrying device), a cutter 1, an anvil roll a turn drum D, a velocity-changeable roller 3, and a conveyance roller 4 (one example of the second carrying device).

The conveyor 5 carries the continuous laminated body S in the introduction velocity V1 while allowing a part of the continuous laminated body S continuing in the carrying direction. Y (FIG. 1B) to be sucked by an attraction section 50.

It is noted that the term "velocity" herein means the conveyance velocity of a work (processing object) and the peripheral velocity of each roll or a pad surface.

The anvil roll 2 at the downstream of the conveyor 5 is rotated at a drum velocity V2 higher than the introduction velocity V1 of the conveyor 5. The anvil roll 2 carries the continuous laminated body S at the introduction velocity V1 of the conveyor 5 by allowing the peripheral surface 2f to suck the tip end S1 of the continuous laminated body S while allowing the tip end S1 of the continuous laminated body S to slip over the peripheral surface 2f.

Specifically, the anvil roll 2 sucks the tip end S1 of the continuous laminated body S by the retention vacuum 2b while rotating at a fixed drum velocity V2 higher than the introduction velocity V1 at which the continuous laminated body S is supplied from the conveyor 5 to the anvil roll 2.

The tip end S1 of the continuous laminated body S introduced to the anvil roll 2 at the introduction velocity V1 is continuous from the continuous laminated body and thus slips over the peripheral surface 2f of the anvil roll 2. Thus, when the continuous laminated body S is introduced to the anvil roll 2, the velocity at which the continuous laminated body S is carried on the anvil roll 2 is the introduction velocity V1 of the conveyor 5.

The cutter 1 intermittently cuts the tip end S1 introduced on the anvil roll 2 of the continuous laminated body S continuing in the carrying direction V with a predetermined interval in the carrying direction Y to sequentially generate a plurality of absorbing bodies 20.

Specifically, the cutter 1 cuts the tip end of the continuous laminated body introduced on the anvil roll 2 to generate a precedent absorbing body 20, and then cuts the tip end of the continuous laminated body newly introduced on the anvil roll 2 to generate a subsequent absorbing body 20.

The anvil roll 2 carries the absorbing body 20 (FIG. 1B) generated by cutting the tip end S1 of the continuous laminated body S along the peripheral surface 2f at the drum velocity V2 to thereby separate the absorbing body 20 from the continuous laminated body S in the carrying direction Y.

Specifically, as shown in FIG. 1B, the tip end S1 that has been cut and released from the continuous laminated body S is carried at the drum velocity V2 of the anvil roll 2, thereby increasing a distance between the already-cut tip end S1 (the absorbing body 20) and the subsequent not-yet-cut tip end S1 of the continuous laminated body S. In other words, an increased distance is caused between the continuous laminated body S carried on the anvil roll at the introduction velocity V1 and the already-cut tip end S1 carried at the drum velocity V2 higher than the introduction velocity V1.

In FIG. 2, the anvil roll 2 includes a retention vacuum 2b. The retention vacuum 2b allows the anvil roll 2 to retain the tip end S1 of the continuous laminated body S before the tip end S1 is cut by the cutter 1 that severs an individual tip end from the continuous laminated body S. Furthermore, the anvil roll 2 is allowed to continuously retain the absorbing body 20 obtained by cutting the tip end S1 by the cutter 1 until the absorbing body 20 is delivered to the retention pad P of the turn drum D.

Although a vacuum area is a well-known structure, the vacuum area is provided to suck the continuous laminated body S or the absorbing body 20 by the retention vacuum 2b in a predetermined area of the anvil roll 2.

The turn drum D at the downstream of the anvil roll 2 receives, from the anvil roll 2, the absorbing body 20 that is a cut-off individual piece of the continuous laminated body S. The turn drum D has the drum velocity V2 set to be equal to the drum velocity V2 of the anvil roll 2.

As shown in FIG. 2, the turn drum D includes a plurality of retention pads P. This retention pad P receives the absorbing body 20 from the anvil roll 2, and then turns the absorbing body 20 around the normal line L of the turn drum D to thereby change the posture of the received absorbing body 20.

Specifically, the turn drum D sequentially receives the respective absorbing bodies 20 from the anvil roll 2 via a plurality of retention pads P. Thereafter, the turn drum D turns the retention pad P by 90° around the normal line L of the turn drum D while carrying the absorbing bodies 20 at the fixed drum velocity V2. This results in the change of the postures of the absorbing bodies 20 together with the retention pads P by 90°.

The posture-changed absorbing bodies 20 are delivered from the turn drum D to a velocity-changeable roller 4 at the downstream.

The retention pad P may include a suction device (not shown). The suction device attracts the absorbing bodies 20 by vacuum from many suction holes formed in the pad surface, for example.

Figure 3B:
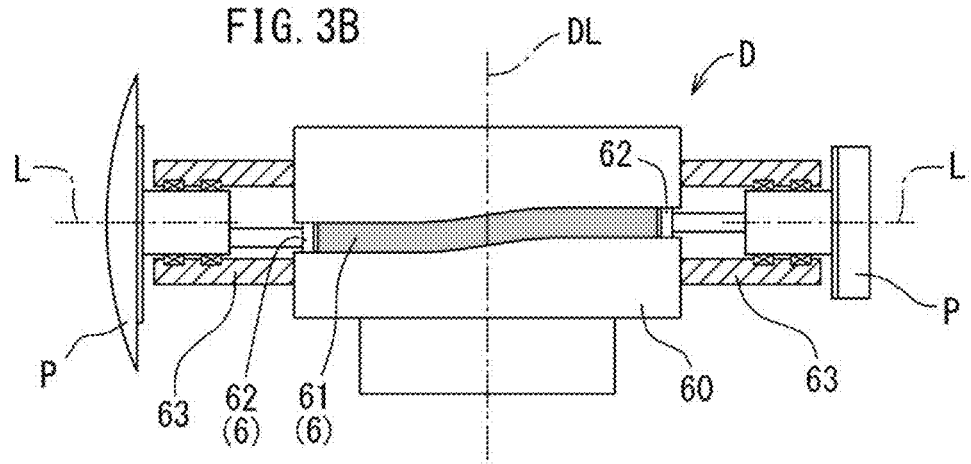
FIG. 3B is a schematic cross-sectional view illustrating a part; of the drum.

As shown in FIG. 3A and FIG. 3B, the turn drum D includes a turn mechanism 6 that independently turns the corresponding retention pad P on the turn drum D as is well known.

The turn mechanism 6 may be composed of a cam follower 62 and a cam groove 61 formed in the peripheral surface of the fixed drum 60 of the turn drum D, for example. Each retention pad P is supported to a rotation drum 63 so that the retention pad can be turned around the normal line L.

The rotation drum 63 is supported so as to be rotatable around the axis line DL to revolve around the fixed drum 60.

It is noted that, in FIG. 2, FIG. 3A, FIG. 3B, FIG. 6, and FIG. 7, the cam groove 61 is colored gray.

The conveyance roller 4 of FIG. 2 is arranged at the downstream of the velocity-changeable roller 3 which receives the absorbing body 20 from the turn drum D. The conveyance roller 4 has an arrangement velocity V3 and carries an exterior material 21.

The velocity-changeable roller 3 is arranged between the conveyance roller 4 and the turn drum D. The velocity-changeable roller 3 at a receiving position R1 is configured to allow a velocity-changeable pad 30 (30A, 30B) to receive the absorbing body 20 from the retention pad P of the turn drum D. Thereafter, the velocity-changeable pads 30A and 30B are configured, at a delivery position R2, to arrange the absorbing body 20 onto the exterior material 21 carried by the conveyance roller 4.

Specifically, at the receiving position R1 where the velocity-changeable pad 30 is abutted to the retention pad P via the absorbing body 20, the velocity-changeable roller 3 (velocity-changeable pad 30) receives the absorbing body 20 from the turn drum D.

Thereafter, at the delivery position R2 where the velocity-changeable pad 30 is abutted to the conveyance roller 4 via the absorbing body 20, the velocity-changeable pad 30 arranges the absorbing body 20 on the exterior material 21 of a wearable article carried by the conveyance roller 4 (one example of the carrying device).

The exterior materials 21 have the longitudinal direction in the carrying direction Y and are continuous in the carrying direction Y. It is noted that the conveyance roller 4 may be a conveyance conveyor.

The conveyance roller 4 may have the arrangement velocity V3 set to be lower than the drum velocity V2 of the turn drum D.

Next, the following section will describe the detailed configuration of the velocity-changeable roller 3.

Figure 4A:
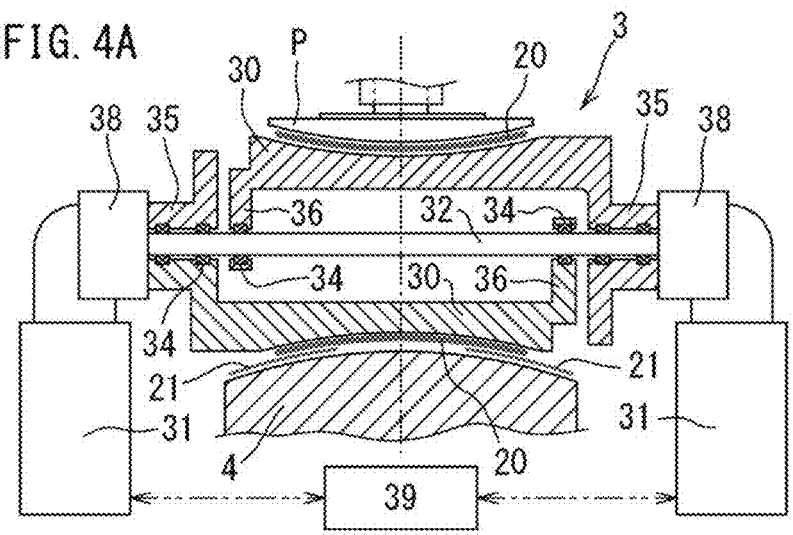
FIG. 4A is a cross-sectional view illustrating one example of a velocity-changeable roller.

As shown in FIG. 4A, the velocity-changeable roller 3 has two (or a plurality of) velocity-changeable pads 30 and a pair of servo motors 31, each servo motor 31 being connected to the corresponding pad 30, for example.

When the arrangement velocity V3 of the conveyance roller 4 at the downstream of the velocity-changeable roller 3 of FIG. 2 is set; to be lower than the drum velocity V2 of the turn drum D, the servo motor 31 may set, in a section from the receiving position R1 to the delivery position R2, the velocities of the respective pads of the velocity-changeable roller 3 to be reduced from the drum velocity V2 of the turn drum D to the arrangement velocity V3 of the conveyance roller 4.

At the delivery position R2, the absorbing body 20 is arranged from the pad 30 of the velocity-changeable roller 3 onto the exterior material 21 carried by the conveyance roller 4.

Specifically at the receiving position R1, the respective pads 30 of the velocity-changeable roller 3 receive the absorbing bodies 20 from the turn drum D at the drum velocity V2. Thereafter, the respective pads 30 rotate and decelerate to the arrangement velocity V3 until the pads 30 reach the delivery position R2. The respective pads 30 are configured, at the delivery position R2, to arrange the bodies 20 on the exterior material 21 on the conveyance roller 4 at the arrangement velocity V3. After the arrangement, the respective pads 30 rotate and accelerate to the drum velocity V2 until the pads 30 reach the receiving position R1.

In FIG. 4A, the velocity-changeable roller 3 includes one long supporting shaft 32 in the axial direction. A pair of velocity-changeable pads 30 is rotated around this supporting shaft 32.

Each velocity-changeable pad 30 is configured so that, at the corresponding end of the supporting shaft 32, the first and second bearing sections 35 and 36 are supported via the bearings 34. This allows a pair of velocity-changeable pads 30 to be rotated around the supporting shaft 32 without being mutually restricted.

The first bearing section 35 is continuously provided with the velocity-changeable pad 30 that extends along the supporting shaft 32. The surface of the pad 30 in the longitudinal direction may be a concave shape toward the supporting shaft 32. In this case, the pad 30 may smoothly extend along the shape of the retention pad P of the turn drum D such as the circular arc-like one.

Figure 4B:
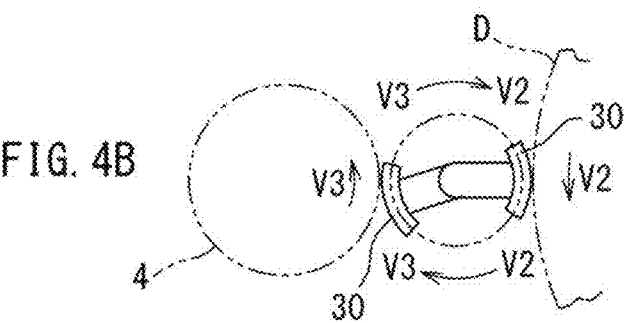
FIG. 4B to FIG. 4D each illustrates the operation of the roller.

As shown in FIG. 4B, the pad 30 may have a circular arc-like side face, for example.

Each bearing section 35 is connected to a servo motor 31 via a gear 38. Thus, the pads 30 are accelerated and decelerated by the change of the rotation velocity of the respective servo motors 31.

Both of the servo motors 31, 31 are rotation-controlled by a control device 39.

The control device 39 includes a storage device to store the relation between the phase (a rotation position) of the relation pad 30 relative to the reference point (e.g., the receiving position R1) and the rotation velocity of the servo motor 31 or the peripheral velocity of the pad 30. This storage device stores therein the respective relations for the standard size (M size) (which will be described later) as well as L size and/or XL size.

Next, the following section will describe one example of the operation of the pad 30 based on the velocity change of the pair of the servo motors 31 in the case where the arrangement velocity V3 of the conveyance roller 4 of FIG. 2 is lower than the drum velocity V2 of the turn drum D. The operation of this servo motor 31 is controlled by the control device 39.

Figure 4C:
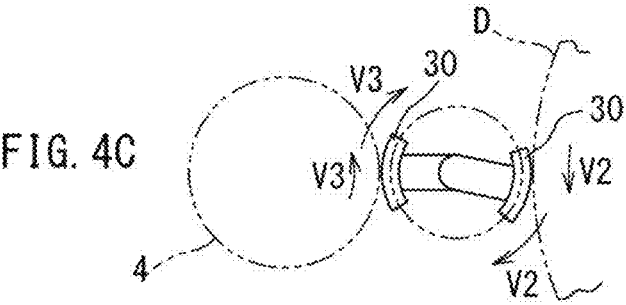
Figure 4D:
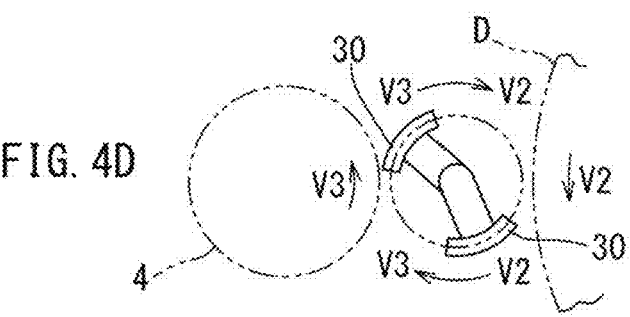

As shown in FIG. 4B to FIG. 4D, the pads 30, 30 are decelerated or accelerated by the respective servo motors 31 (FIG. 4A) at least one time per one rotation of the pads 30 to thereby have a different velocity cyclically.

Specifically, the pad 30 has the same velocity as the drum velocity V2 of the turn drum D when the pad 30 is at the receiving position R1 (FIG. 2) at which the pad 30 is abutted to the turn drum D and is in the vicinity of the receiving position R1. On the other hand, the pad 30 has the same velocity as the arrangement velocity V3 of the conveyance roller 4 when the pad 30 is at the delivery position R2 (FIG. 2) at which the pad 30 is abutted to the conveyance roller 4 and is in the vicinity of the delivery position R2. The arrangement velocity V3 is set to be lower than the drum velocity V2.

In an area from the receiving position R1 to the delivery position R2, the pad 30 is rotated while being decelerated to a velocity from the drum velocity V2 to the arrangement velocity V3. This provides a reduced distance between the precedent absorbing body 20 and the subsequent absorbing body 20, as has been well known.

In other words, in one rotation of the pad 30 from the receiving position R1 to the delivery position R2, the pad 30 has the same velocity as the drum velocity V2 of the turn drum D at the receiving position R1 and in the vicinity thereof; thereafter, the pad 30 is decelerated to have a velocity lower than the drum velocity V2; and, when the pad 30 enters a section near the delivery position R2, the pad 30 is decelerated to have the same velocity as the arrangement velocity V3 of the conveyance roller 4.

As shown in FIGS. 2 and 4B to FIG. 4D, the pad 30 at the delivery position R2 arranges the absorbing body 20 to the exterior material 21 and, after having passed a section in the vicinity of the delivery position R2, the pad 30 is accelerated to have a velocity higher than the arrangement velocity V3 of the conveyance roller 4.

Thereafter, when the pad 30 enters a section in the vicinity of the receiving position R1, the pad 30 is further accelerated to have the drum velocity V2 of the turn drum D.

After being accelerated to have the drum velocity V2, the pad 30 receives the absorbing body 20 from the turn drum D similarly rotating at the drum velocity V2 at the receiving position R1. It is noted that the absorbing body 20 is not shown in FIG. 4B to FIG. 4D.

Next, the following section will describe one example of the manufacture method of the absorbing body 20.

First, the following section will describe a method of manufacturing a wearable article of an XL-size (or a large size) as one example of the first size. This manufacture method includes an introduction step, a slip step, a cutting step, a separation step, a first transfer step, a posture change step, a second transfer step, a velocity change step, a carrying step, and an arrangement step as described below.

In FIG. 2, in the introduction step, the continuous laminated body S continuing in the carrying direction Y (FIG. 1B) to be later used as the absorbing bodies 20 is introduced at the introduction velocity V1 (V11) form the conveyor 5 to the anvil roll 2.

In the slip step after the introduction, the continuous laminated body S is carried at the introduction velocity V1, with the tip end S1 of the continuous laminated body S being sucked by the retention vacuum 2b on the peripheral surface 2f of the anvil roll 2 rotating at the drum velocity V2 higher than the introduction velocity V1 in a state where the tip end S1 of the continuous laminated body S slips over the peripheral surface 2f of the anvil roll 2.

In the cutting step, the tip end S1 of the continuous laminated body S introduced on the anvil roll 2 at the introduction velocity V1 is intermittently cut by the cutter 1 to sequentially obtain the absorbing bodies 20.

In the separation step after the cutting step, the absorbing body 20 is carried at the drum velocity V2 along the peripheral surface 2f of the anvil roll 2 to thereby separate the absorbing body 20 in the carrying direction from the continuous laminated body S.

Specifically, the cut tip end S1 of the continuous laminated body S is released from the continuous laminated body S due to the cutting operation and is carried at the drum velocity V2 higher than the introduction velocity V1. Thus, a distance between the already-cut tip end S1 (the absorbing body 20) and a following tip end S1 of the continuous laminated body S increases, the following tip end being carried at the introduction velocity V1 before being cut at the cutting step.

In the first transfer step after the separation step, the respective separated absorbing bodies 20 are sequentially delivered from the anvil roll 2 to the respective retention pads P of the turn drum D. Specifically, the absorbing body 20 carried by the anvil roll 2 at the drum velocity V2 is delivered to the retention pad P of the turn drum D similarly rotated at the drum velocity V2.

In the posture change step after the first transfer step, the respective retention pads P of a turn drum D, which receive the absorbing bodies 20, are allowed to rotate around the axis line DL of the turn drum D (FIG. 3B) at the fixed drum velocity V2 during which each retention pad P on the turn drum D is turned by 90° around the normal line L of the turn drum D. This turning causes the postures of the respective absorbing bodies 20 to be changed together with the respective retention pads P.

In the second transfer step after the posture change, the absorbing bodies 20 whose postures have been changed are transferred at the receiving position R1 at the drum velocity V2 from the respective retention pads P of the turn drum D to the respective velocity-changeable pads 30A and 30B of the velocity-changeable roller 3.

Specifically, during the period from the first transfer step to the second transfer step, the retention pad P of the turn drum on which the absorbing body 20 is retained is turned by 90° around the normal line L of the turn drum D and the posture of the absorbing body 20 is changed; thereafter, the absorbing body 20 is transferred to the pad of the velocity-changeable roller 3 at the receiving position R1.

In the velocity change step after the second transfer step, the velocity of the velocity-changeable roller 3 is changed from the drum velocity V2 to the arrangement velocity V3 until the velocity-changeable roller 3 is moved from the receiving position R1 to the delivery position R2.

Specifically, the velocity-changeable pad 30 of the velocity-changeable roller 3 at the receiving position R1 receives the absorbing body 20 at the drum velocity V2 and is subsequently decelerated to the arrangement velocity V3 lower than the drum velocity V2 until the pad 30 reaches the delivery position R2.

Meanwhile, in the carrying step, the exterior material 21 is carried by a carrying device 4 at the arrangement velocity V3 (V31).

In the arrangement step, at the delivery position R2, the absorbing bodies 20 are sequentially arranged on the exterior material 21 carried by the carrying device 4.

Specifically, the velocity-changeable pads 30 of the velocity-changeable roller 3 decelerate from the drum velocity V2 to the arrangement velocity V3, and sequentially arrange, at the delivery position R2, the absorbing bodies 20 on the exterior material 21 similarly carried at the arrangement velocity V3.

The introduction velocity V1 and the arrangement velocity V3 are set depending on the respective sizes of the wearable article. The introduction velocity V1 may be higher than the arrangement velocity V3. On the other hand, the drum velocity V2 of the turn drum D is set to a fixed velocity regardless of the size.

In the case of this example, the drum velocity V2 is set to a fixed velocity higher than the introduction velocity V1 and the arrangement velocity V3 regardless of the size of the wearable article.

Figure 6:
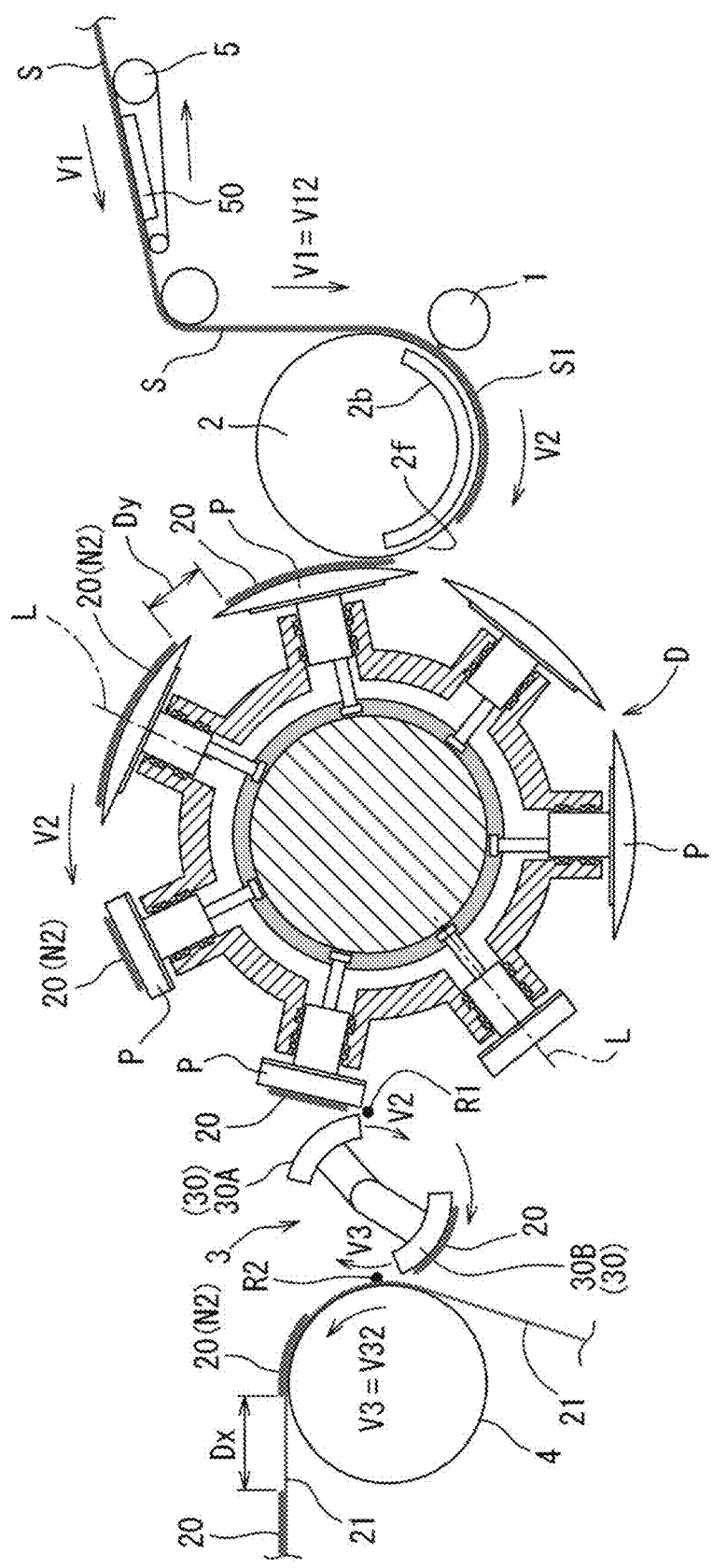
FIG. 6 is a schematic view illustrating the layout in the case where a wearable article of the second size is manufactured.

Next, the following section will describe a method of manufacturing a wearable article of the first size of FIG. 2 and a wearable article of the second size (e.g., L size) of FIG. 6 having a shorter length in the carrying direction than that of the first size.

In order to manufacture the wearable article N1 of the first size, the introduction velocity V1 is set to the first introduction velocity V11 having a high velocity and the arrangement velocity V3 is set to the first the arrangement velocity V31 having a high velocity.

On the other hand, in order to manufacture the wearable article N2 of the second size smaller than the wearable article N1 of the first size, the introduction velocity V1 is set to the second introduction velocity V12 lower than the first introduction velocity V11 and the arrangement velocity V3 is set to the second arrangement velocity V32 lower than the first the arrangement velocity V31.

The drum velocity V2 is set to a fixed velocity regardless of a difference in the size.

Since the drum velocity V2 is set; to a fixed velocity regardless of the size of the wearable article, the absorbing bodies 20 on the turn drum D adjacent to each other in the circumference direction also have a fixed pitch (interval) P1 (FIG. 1B) regardless of the size.

On the other hand, when the size is smaller, the absorbing body 20 also has a shorter length Ly (FIG. 1B) in the carrying direction Y. Thus, the distance Dy (FIG. 6) between the rear end of the precedent absorbing body 20 of the wearable article N2 of the second size and the front end of the subsequent absorbing body 20 is larger than the corresponding distance Dy of the wearable article N1 of the first size.

Furthermore, regardless of the smaller size, the absorbing bodies 20 on the turn drum D still have the fixed pitch P1. Thus, the absorbing bodies 20 which are to be later arranged on the exterior material 21 of FIG. 6 must have a reduced pitch (interval).

Thus, when the manufacture of a wearable article of the second size of FIG. 6 is compared with that of a wearable article of the first size, the deceleration degree of the velocity-changeable pad 30 in an area from the receiving position R1 to the delivery position R2 is increased, and the distance Dx between the rear end of the precedent absorbing body 20 after the posture change and the front end of the subsequent absorbing body 20 after the posture change is reduced (i.e., the pitch is reduced).

In the manufacture of the wearable article of the second size, the second carrying device 4 is set to have the second arrangement velocity V32.

Specifically, in order to manufacture the wearable article of the second size, the velocity-changeable pad 30 receives the absorbing body 20 at the drum velocity V2 at the receiving position R1, and arranges the absorbing body 20 on the exterior material 21 at the second arrangement velocity V32 lower than the first the arrangement velocity V31. Thus, a wearable article of the second size can be manufactured with a narrower distance Dx between absorbing bodies than in the case of the manufacture of the wearable article of the first size, thus providing the accommodation to a size change.

Next, the following section will describe a method of manufacturing a wearable article N3 of the third size (e.g., M size) of FIG. 7 having a further-shorter length in the carrying direction than that of the wearable article of the second size of FIG. 6.

In order to manufacture the wearable article N3 of the third size, the introduction velocity V1 is set to the third the introduction velocity V13 further lower than the second introduction velocity V12. The arrangement velocity V3 is set to the third arrangement velocity V33 further lower than the second arrangement velocity V32. On the other hand, the drum velocity V2 is set to a fixed velocity regardless of the size.

Since the drum velocity V2 is fixed regardless of the size of the wearable article, the absorbing bodies 20 on the turn drum D also have a fixed pitch (interval) P1 regardless of the size.

On the other hand, when the size is further smaller, the absorbing body 20 also has a further-shorter length Ly (FIG. 1B) in the carrying direction. Thus, a distance Dy between the rear end of the precedent absorbing body 20 and the front end of the subsequent absorbing body 20 further increases.

The absorbing bodies 20 on the turn drum D have a fixed pitch in spite of the smaller-size wearable article. Thus, a pitch (interval) between the absorbing bodies 20 arranged on the exterior material 21 of FIG. 7 needs to be smaller.

Thus, in the manufacture of the wearable article of the third size of FIG. 7 in comparison with the manufacture of the wearable article of the second size, the deceleration of the velocity-changeable pad 30 moving from the receiving position R1 to the delivery position R2 further increases, and a distance Dx (or a pitch) between the rear end of the precedent absorbing body 20 after the posture change and the front end of the subsequent; absorbing body 20 after the posture change is further reduced.

In the manufacture of the wearable article of the third size, the second carrying device 4 is set to the third arrangement velocity V33.

Specifically in the case of the manufacture of the wearable article of the third size, the velocity-changeable pad 30 receives the absorbing body 20 at the drum velocity V2 at the receiving position R1 and arranges the absorbing body 20 on the exterior material 21 at the third arrangement velocity V33 lower than the second arrangement velocity V32. Thus, in the manufacture of the wearable article of the third size, the distance Dx between the precedent and subsequent absorbing bodies 20 is narrower than the corresponding distance Dx between such absorbing bodies 20 in the manufacture of the wearable article of the second size.

Figure 5:
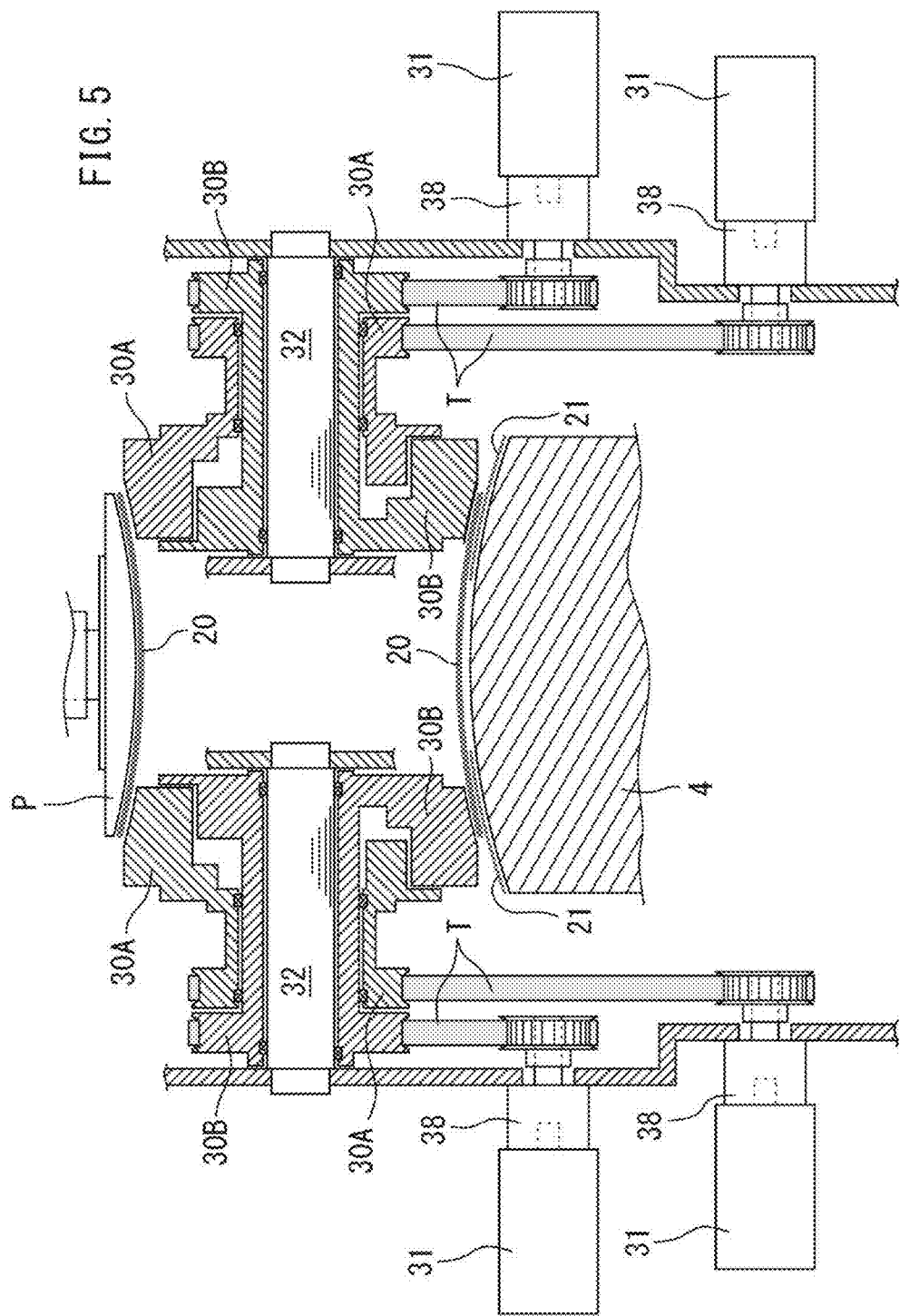
FIG. 5 is a cross-sectional view illustrating another example of the velocity-changeable roller.

Next, the following section will describe another example of the velocity-changeable roller 3 of FIG. 5.

In FIG. 5, the velocity-changeable roller 3 includes a pair of the first velocity-changeable pads 30A to retain both ends of one absorbing body 20 in the longitudinal direction and a pair of the second velocity-changeable pads 30B to retain both ends of another absorbing body 20 in the longitudinal direction Specifically one pad of the pair of the first (second) velocity-changeable pads 30A (30B) retains one end of the absorbing body and another pad of the first (second) pair of velocity-changeable pads 30A (30B) retains another end of the same absorbing body.

As shown in FIG. 5, each velocity-changeable pad 30A and 30B may be rotated by the corresponding servo motor 31 via the corresponding gear 38 and a corresponding timing belt T.

The velocity-changeable pad 30B may be arranged around the supporting shaft 32. The velocity-changeable pad 30A may be arranged outside the velocity-changeable pad 30B. The velocity-changeable pads 30A and 30B may have pulley portions having the same diameter.

The pair of velocity-changeable pads 30A (30B) that retains both ends of the absorbing body 20 is rotated around the supporting shaft 32 to arrange the absorbing body 20 on the exterior material 21 carried by the second the carrying device 4.

The respective pads may include a suction device (not shown). The suction device attracts an end of the absorbing body 20 by the vacuum through many suction holes formed in the surfaces of the respective pads.

As described above, a preferred embodiment has been described with reference to the drawings. However, various changes and modifications may be clear for those skilled in the art in view of this specification within an obvious scope.

For example, in a section from the receiving position R1 to the delivery position R2, the rotation velocity of each servo motor 31 was changed to thereby decelerate of the corresponding velocity-changeable pad 30 of the velocity-changeable roller 3. However, the velocity-changeable pad 30 of the velocity-changeable roller 3 may be accelerated instead of deceleration.

Thus, the change and modification as described above are interpreted as being within the scope of the present invention determined based on claims.

INDUSTRIAL APPLICABILITY

The present invention can be applied to the manufacture apparatus of an absorbing core of a disposable wearable article.

REFERENCE SIGNS LIST

1: Cutter
2: Anvil roll 2b: Retention vacuum 2f: Peripheral surface 20: Absorbing body 21: Exterior material 22: Torso member 24: Absorbing core
3: Velocity-changeable roller 30: Velocity-changeable pad 30A: First velocity-changeable pad 30B: Second velocity-changeable pad 31: Servo motor 32: Supporting shaft 34: Bearing 35: First bearing section 36: Second bearing section 38: Gear 39: Control device
4: Second carrying device (Conveyance roller)
5: First carrying device (Conveyor) 50: Attraction section
6: Turn mechanism 60: Fixed drum 61: Cam groove 62: Cam follower 63: Rotation drum
D: Turn dr Dy: Distance Dx: Distance
P: Retention pad R1: Receiving position R2: Delivery position
V1: Introduction velocity V2: Drum velocity V3: Arrangement velocity
S: Continuous laminated body S1: Tip end
L: Normal line DL: Axis line Y: Carrying direction

The invention claimed is:

1. A method for manufacturing a disposable wearable article in which an absorbing body overlaps an external material, the method comprising:
an introduction step of introducing a continuous laminated body, which extends in a carrying direction, to an anvil roll at an introduction velocity, the continuous laminated body being to be used as absorbing bodies;
a slip step of carrying the continuous laminated body at the introduction velocity, the slip step being performed by sucking a tip end of the continuous laminated body on a peripheral surface of the anvil roll rotating at a drum velocity higher than the introduction velocity, with the tip end of the continuous laminated body slipping over the peripheral surface of the anvil roll;
a cutting step of intermittently cutting the tip end of the continuous laminated body on the anvil roll to thereby sequentially obtain the absorbing bodies;
a separation step of carrying the absorbing bodies, which have been cut in the cutting step, at the drum velocity along the peripheral surface of the anvil roll to thereby separate the absorbing bodies from the continuous laminated body in the carrying direction;
a first transfer step of sequentially transferring the absorbing bodies, which have been separated in the separation step, from the anvil roll to respective retention pads P of a turn drum;
a posture change step of allowing the retention pads of the turn drum to rotate around an axis line of the turn drum at a fixed velocity that equals the drum velocity, the posture change step allowing each of the retention pads on the turn drum to turn around a normal line of the turn drum to thereby change a posture of the absorbing bodies together with the retention pads;
a second transfer step of transferring the absorbing bodies from the retention pads of the turn drum to respective velocity-changeable pads and of a velocity-changeable roller at a receiving position at the drum velocity;
a velocity change step of changing a velocity of the velocity-changeable roller from the drum velocity to an arrangement velocity until the velocity-changeable roller reaches a delivery position from the receiving position;
a carrying step of allowing a carrying device to carry an external material at the arrangement velocity; and
an arrangement step of sequentially arranging, at the delivery position, the absorbing bodies over the exterior material carried by the carrying device,
wherein:
the introduction velocity and the arrangement velocity are each set to a respective velocity depending on a size of a wearable article; and
the drum velocity of the turn drum is set to a fixed velocity regardless of the size of the wearable article.

2. The manufacturing method according to claim 1, wherein:
the drum velocity is set to a fixed velocity regardless of the size of the wearable article, the fixed velocity being higher than the introduction velocity and the arrangement velocity.

3. The manufacturing method according to claim 1, wherein:
the method manufactures a first-size wearable article and a second-size wearable article, the second-size wearable article having a shorter length in the carrying direction than that of the first-size wearable article;
when the first-size wearable article is manufactured, the introduction velocity is set to a first introduction velocity having a high velocity, and the arrangement velocity is set to a first arrangement velocity having a high velocity;
when the second-size wearable article is manufactured, the introduction velocity is set to a second introduction velocity lower than the first introduction velocity, and the arrangement velocity is set to a second arrangement velocity lower than the first arrangement velocity; and
the drum velocity is set to a fixed velocity regardless of the size of the wearable article.

4. The manufacturing method according to claim 3, wherein:
the method manufactures a third-size wearable article having a length in the carrying direction shorter than that of the second-size wearable article; and
when the third-size wearable article is manufactured, the introduction velocity is set to a third introduction velocity lower than the second introduction velocity,
the drum velocity is set to a fixed velocity regardless of the size of the wearable article, and
the arrangement velocity is set to a third arrangement velocity lower than the second arrangement velocity.

5. The manufacturing method according to claim 1, wherein:
in a section from the receiving position to the delivery position, each of the velocity-changeable pads of the velocity-changeable roller is decelerated or accelerated by changing a rotation velocity of a corresponding servo motor.

6. An apparatus for manufacturing a disposable wearable article in which an absorbing body overlaps an exterior material, the apparatus comprising:
- a first carrying device configured to carry a continuous laminated body, which extends in a carrying direction, at a variable introduction velocity based on a size of the wearable article, the continuous laminated body being to be used as absorbing bodies;
- an anvil roll configured to:
  - rotate at a fixed drum velocity higher than the variable introduction velocity,
  - suck a tip end of the continuous laminated body on a peripheral surface of the anvil roll while allowing the tip end of the continuous laminated body to slip over the peripheral surface, thereby carrying the continuous laminated body at the variable introduction velocity, and
  - carry absorbing bodies, which are obtained by intermittently cutting the tip end of the continuous laminated body, along the peripheral surface at the drum velocity higher than the variable introduction velocity to thereby separate the absorbing bodies from the continuous laminated body in the carrying direction;
- a cutter configured to intermittently cut the tip end of the continuous laminated body on the anvil roll to thereby sequentially generate the absorbing bodies;
- a turn drum configured to sequentially receive the absorbing bodies from the anvil roll via respective retention pads of the turn drum, the turn drum being configured to carry the absorbing bodies at a fixed velocity that equals the drum velocity while each of the retention pads turns around a normal line of the turn drum to thereby change a posture of the absorbing bodies together with the retention pads;
- a second carrying device configured to carry an exterior material at a variable arrangement velocity based on the size of the wearable article; and
- a velocity-changeable roller configured to receive the absorbing bodies from the retention pads of the turn drum via respective velocity-changeable pads of the roller at a receiving position, the velocity-changeable pads being configured to transfer, at a delivery position, the absorbing bodies to the exterior material carried by the second carrying device.

7. The manufacturing apparatus according to claim 6, wherein:
the turn drum includes turn mechanisms configured to independently turn the respective retention pads on the turn drum.

8. The manufacturing apparatus according to claim 6, wherein:
the velocity-changeable roller includes: a pair of first velocity-changeable pads configured to retain both ends in a longitudinal direction of a precedent absorbing body among the absorbing bodies; and a pair of second velocity-changeable pads configured to retain both ends in the longitudinal direction of a subsequent absorbing body among the absorbing bodies.

* * * * *